United States Patent [19]

Perouse et al.

[11] Patent Number: 5,346,115
[45] Date of Patent: Sep. 13, 1994

[54] SURGICAL STAPLE INSERTER

[75] Inventors: Eric Perouse, 176 Parc de Cassan, 95290 L'Isle Adam, France; Thierry Richard, 71 Boulevard Arago, 75013 Paris, France; Yves Arnissolle, Saint Genis-Laval, France

[73] Assignees: Eric Perouse, L'Isle Adam; Thierry Richard, Paris; Laboratoire Perouse Implant, Bornel, all of France

[21] Appl. No.: 966,186

[22] PCT Filed: Mar. 30, 1992

[86] PCT No.: PCT/FR92/00287
§ 371 Date: Jan. 29, 1993
§ 102(e) Date: Jan. 29, 1993

[87] PCT Pub. No.: WO92/17117
PCT Pub. Date: Oct. 15, 1992

[30] Foreign Application Priority Data

Mar. 29, 1991 [FR] France ................... 9103913

[51] Int. Cl.⁵ .......................................... A61B 17/115
[52] U.S. Cl. ........................................ 227/179; 227/19
[58] Field of Search ................ 227/19, 179, 175, 178

[56] References Cited

U.S. PATENT DOCUMENTS 3,519,187  7/1970  Kapitanov .
4,304,236 12/1981  Conta et al. .
4,872,874 10/1989  Taheri .
4,930,674  6/1990  Barak ............................... 227/179

FOREIGN PATENT DOCUMENTS 2171477  9/1973  France .
2038226  7/1980  United Kingdom .

Primary Examiner—Rinaldi I. Rada
Attorney, Agent, or Firm—Wenderoth, Lind & Ponack

[57] ABSTRACT

A surgical staple inserter for joining two ducts such as a blood vessel and a blood prosthesis. The staple inserter ejects staples in a radial direction relative to the axis of the ducts. In one embodiment, it includes a staple holder surrounded by the prosthesis and containing a series of staples arranged in at least one ring. All the staples are ejected simultaneously. The staple inserter also includes an anvil outside the organic duct, and a device for spacing apart the anvil and the staple holder in relation to their relative working positions. Projections hold the prosthesis in place during the insertion of the staple holder into the ducts.

19 Claims, 12 Drawing Sheets

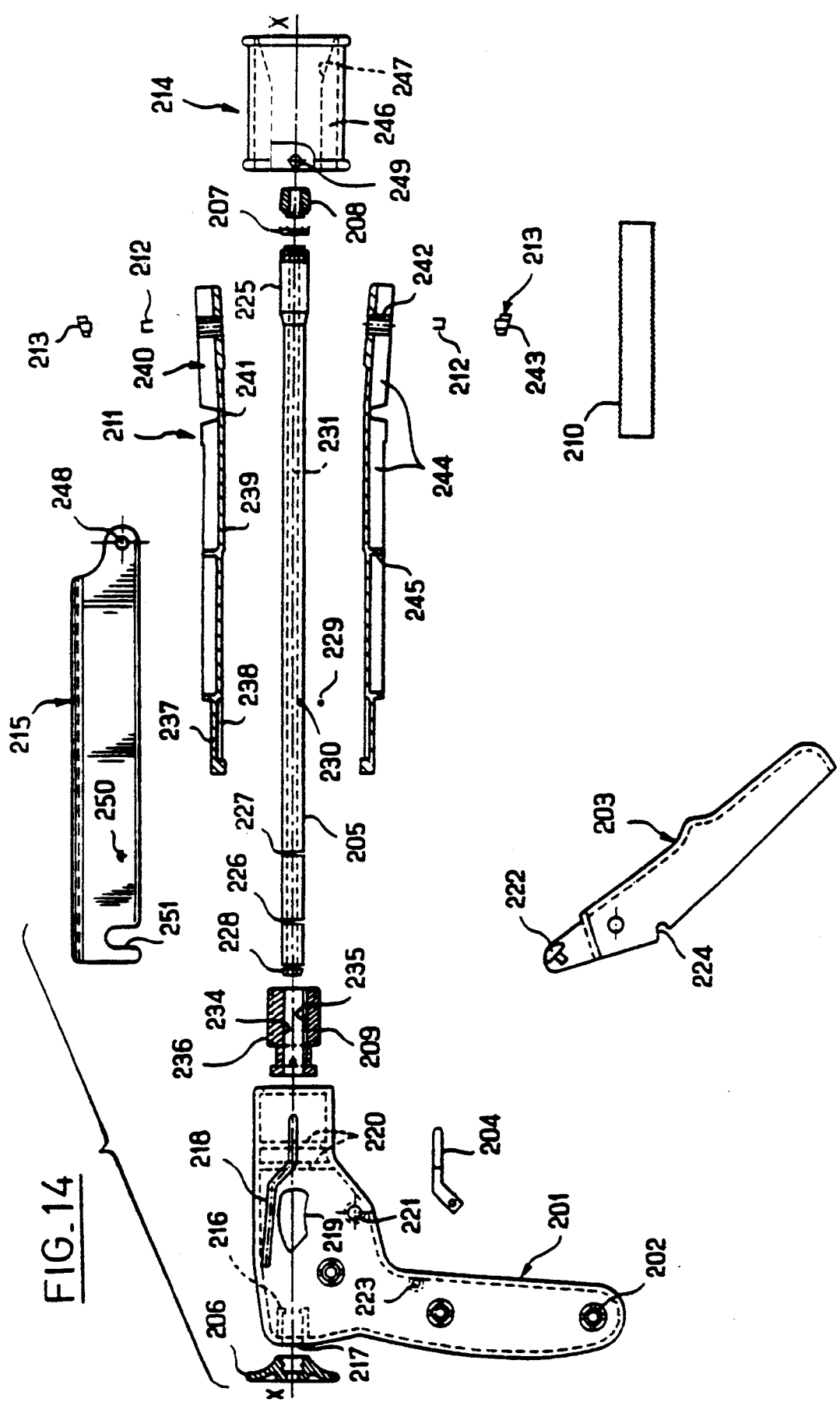

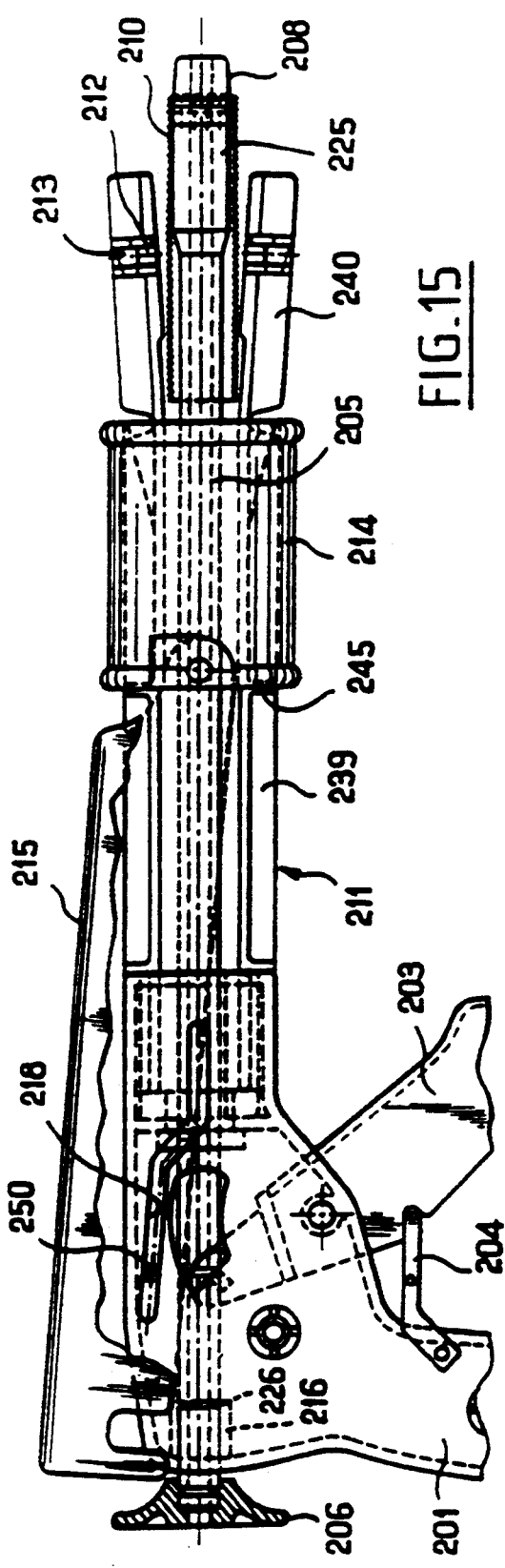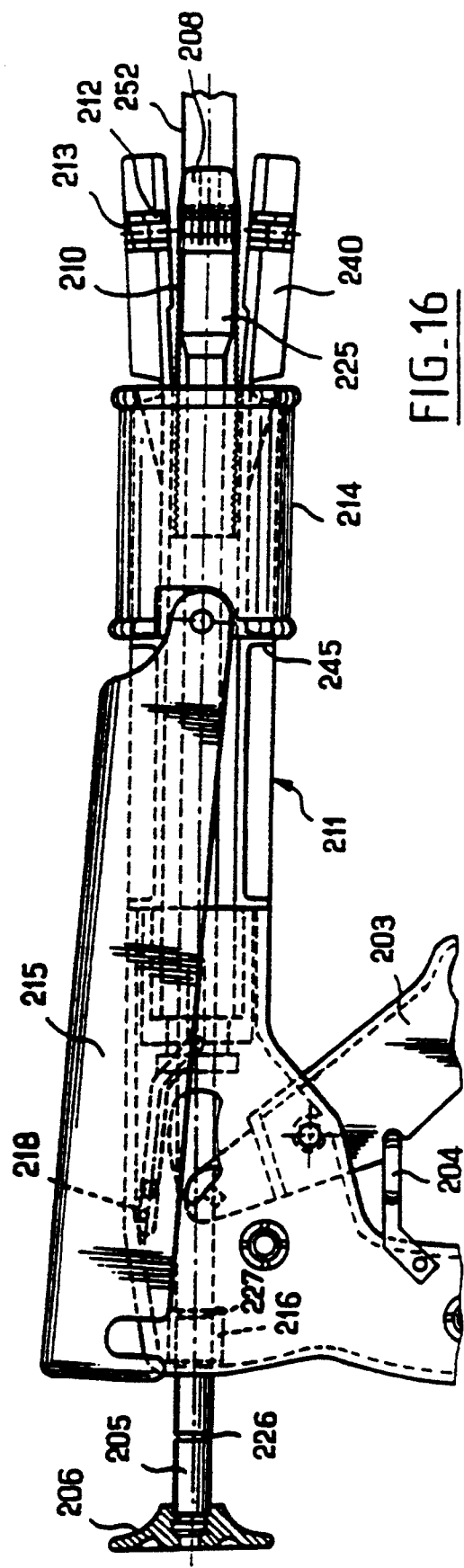

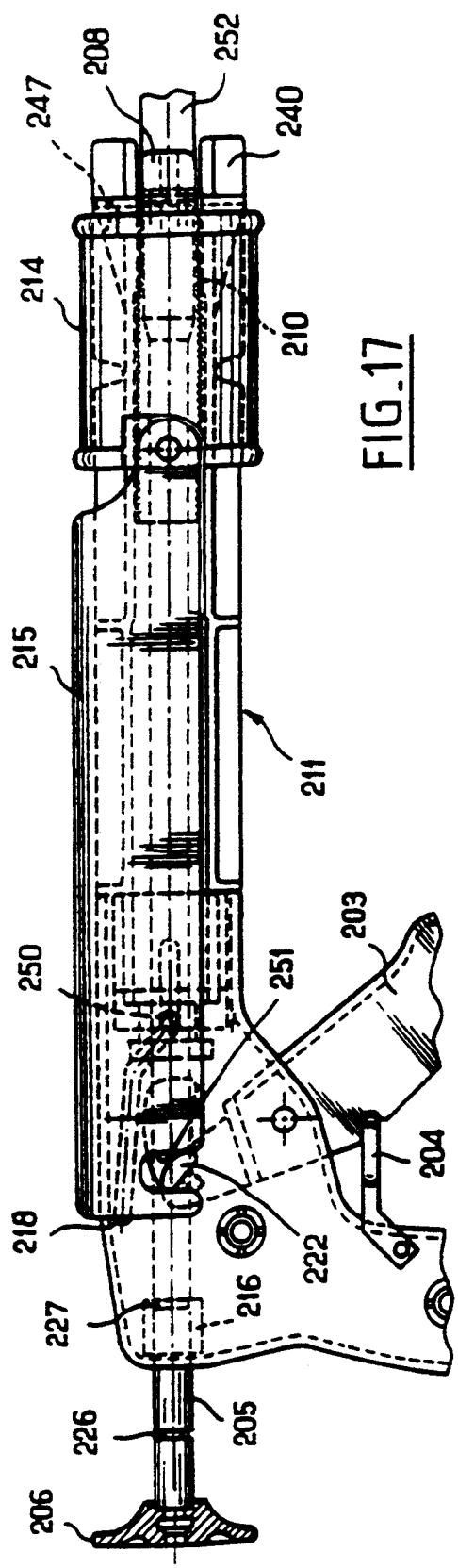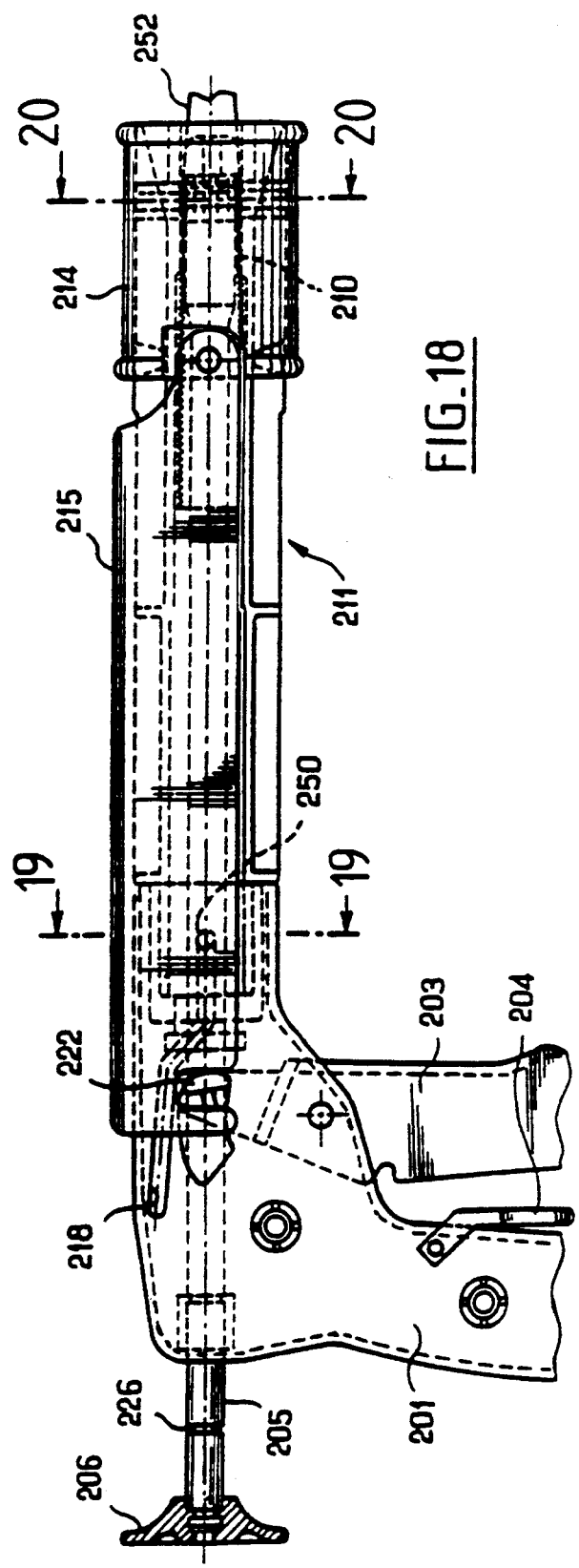
FIG. 17
FIG. 18

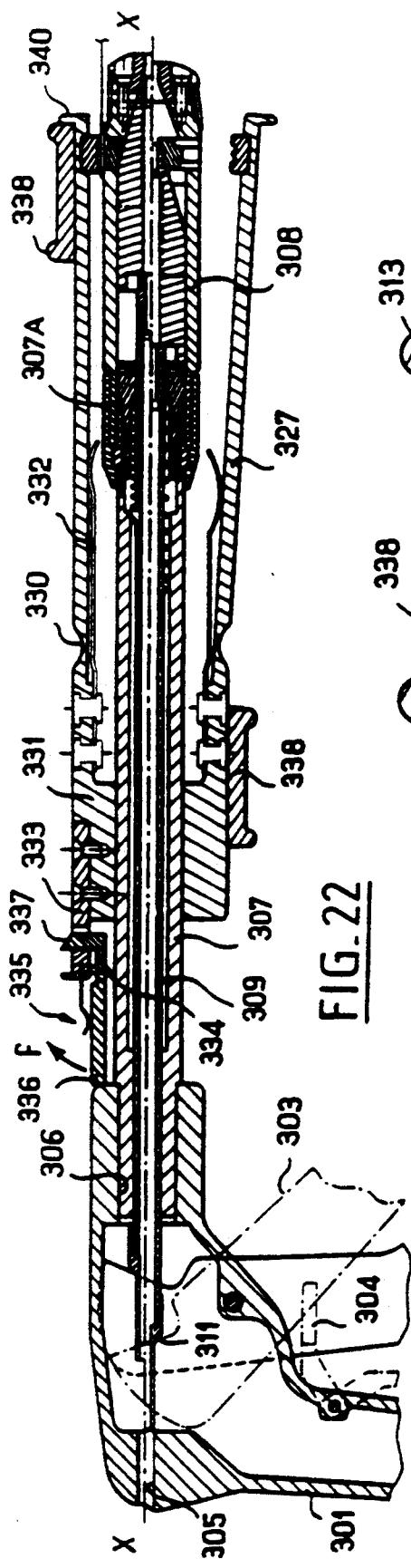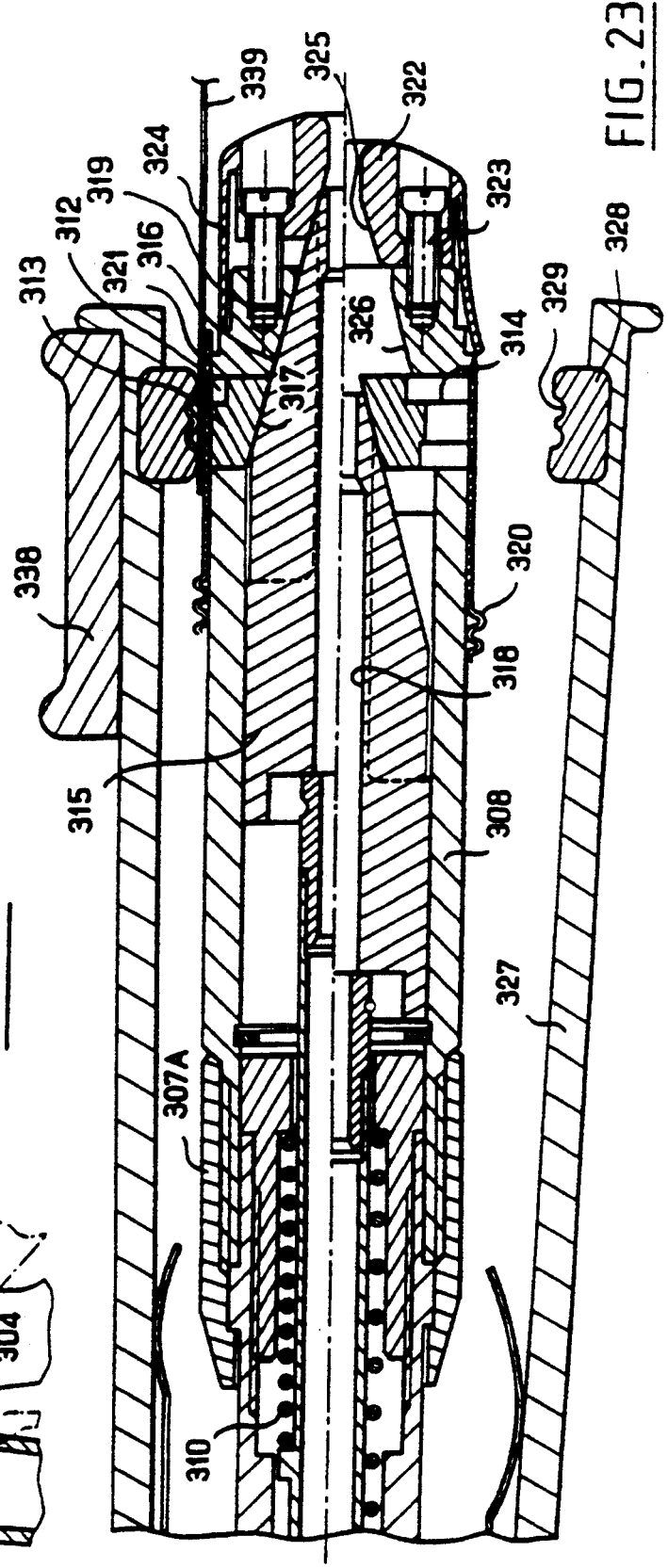

SURGICAL STAPLE INSERTER

BACKGROUND OF THE INVENTION

The invention relates to a surgical staple inserter intended to join two ducts consisting of a vessel and a tubular vessel prosthesis, of the type including a first part, called the internal part, intended to be received inside the ducts, and a second part, called the external part, remaining outside the ducts. One of the two parts of the staple inserter includes a staple holder which contains a series of staples disposed in at least one ring with their points oriented radially, and means for ejecting these staples. The other part of the staple inserter includes an anvil. The staple inserter includes means for radially spacing apart the anvil and the staple holder with respect to their relative working positions.

The human body includes several types of organic ducts, such as for example the organs of the digestive system or of the circulatory system. During a surgical operation, there may be a need to suture two parts of sectioned organic ducts together, for example following partial ablation of the duct.

In the case of vessels, which are difficult to suture, it is known to join a tubular prosthesis to the ends of the vessels. The wall of the prosthesis is more flexible than that of the vessel, which allows easier manipulations. It is thus possible to join the two parts of vessels by first joining a vessel prosthesis end to each of the vessel ends, then by subsequently joining the two vessel prosthesis ends by known manual or mechanical means.

However, in the current art, suturing of the ends of the vessels must be performed manually by stitching.

SUMMARY OF THE INVENTION

The object of the invention is to allow mechanical sutures to be made in a convenient and secure manner by means of staples on relatively rigid organic ducts, such as blood vessels.

For this purpose, the subject of the invention is a surgical staple inserter of the aforementioned type, characterized in that a tubular vessel prosthesis is placed over a portion of the internal part of the staple inserter, and in that points for holding the prosthesis in place project on this internal part.

It is to be noted that the prior art describes staple inserters with rings of staples which have points oriented radially (GB-A-2,038,226, FR-A-2,171,477), but that these known staple inserters do not allow a vessel and a vessel prosthesis to be joined up conveniently inside the human body.

BRIEF DESCRIPTION OF THE DRAWINGS

The invention will be described in more detail hereinbelow with reference to the attached drawings, in which:

FIG. 14 is an exploded view of a second embodiment of the staple inserter according to the invention;

FIGS. 15 to 18 are elevation views partially in section illustrating the operation of the staple inserter in FIG. 14;

FIG. 22 is a longitudinal section of a third embodiment of the staple inserter according to the invention; and FIG. 23 is a similar view, on a larger scale, of the distal end part of the staple inserter in FIG. 22.

DETAILED DESCRIPTION OF THE INVENTION

Figure 1:
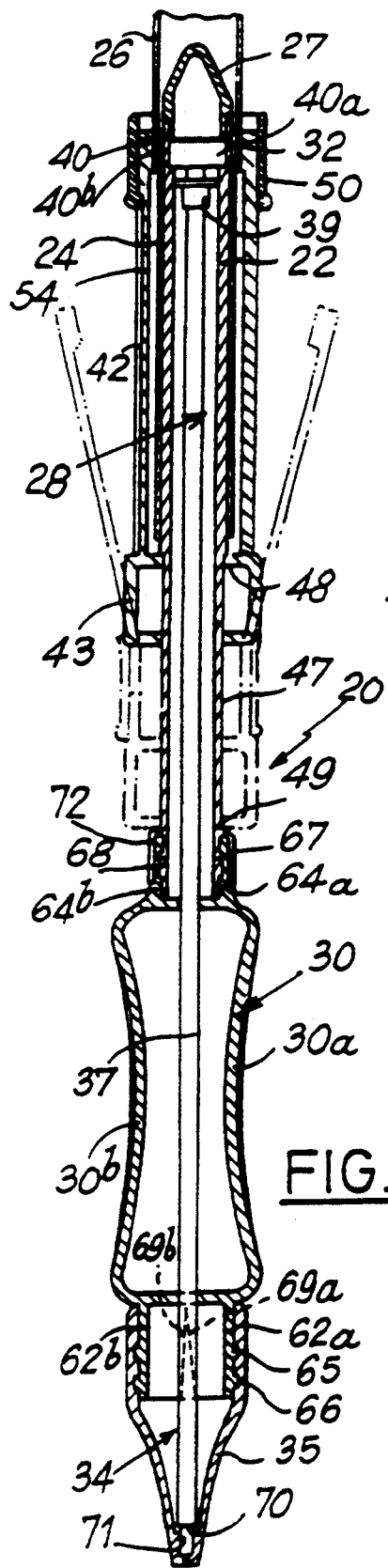
FIG. 1 is a longitudinal section of a staple inserter according to the invention.
Figure 2:
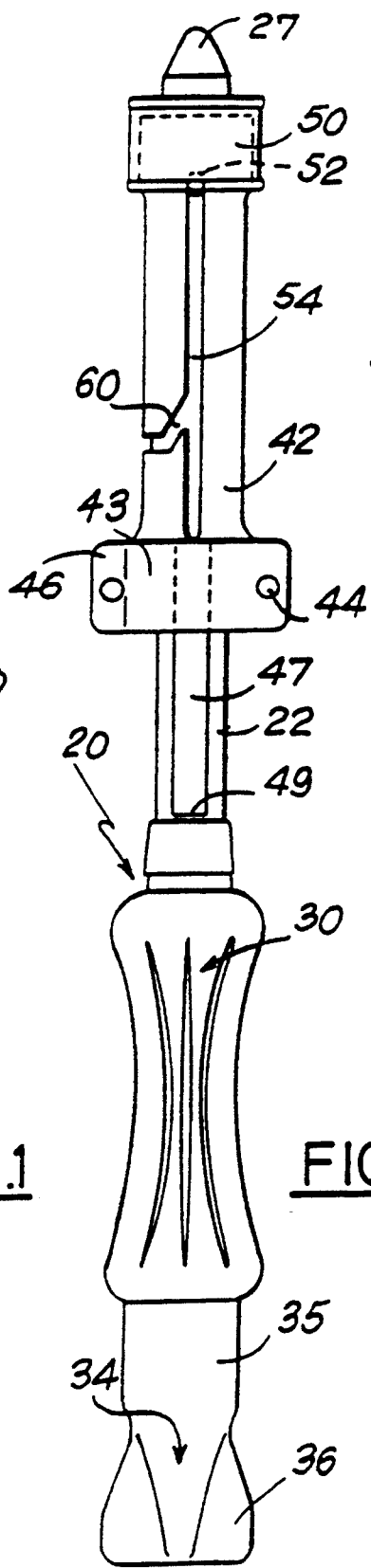
FIG. 2 is an elevation view of a general arrangement of the staple inserter.

The staple inserter 20 of a generally elongate form is seen in FIGS. 1 and 2. It includes a tube 22 whose distal end is received in ducts, namely a prosthesis 24 and an organic duct 26. The prosthesis 24 is placed over the external surface of the tube 22 in order to be stapled to the organic duct 26, for example a vessel, partially covering the prosthesis 24 at the distal end of the tube 22. The distal end of the tube 22 includes a cap 27, pressed or glued into the tube, in the shape of a nose cone facilitating the penetration of the staple inserter 20 into the ducts. The cap 27 and the part of the tube 22 around which the prosthesis 24 and the vessel 26 are placed constitute a part which is internal with respect to ducts 24, 26. The rest of the staple inserter constitutes a part which is external with respect to the ducts 24, 26. The proximal part of the tube 22 is carried by a staple inserter handle 30 consisting of two longitudinal half-handles 30a, 30b.

A staple holder 32 of cylindrical general shape is arranged at the distal end of the tube 22. It includes means for ejecting staples radially, which means will be described subsequently and are represented in detail according to a first embodiment of the staple holder in FIG. 4 and according to a second embodiment of the staple holder in FIG. 9. The means for ejecting staples are controlled by the user by means of a stapling wing nut 34, mounted so as to rotate on the proximal end of the handle 30. The wing nut 34 includes a cap 35 fitted with two operating fins 36 and is connected to the means for ejecting the staples from the staple holder 32 by a linkage comprising a rod 37 connected to the staple holder 32 by a drive nut 39.

An anvil 40 is disposed outside the tube 22, at the staple holder 32, in order to deform the points of the staples which are ejected radially from the staple holder 32. The anvil 40 is shown in more detail in FIGS. 4 and 5 according to a first embodiment and in FIG. 9 according to a second embodiment. In both embodiments, the anvil 40 consists of two anvil sectors 40a, 40b, each carried by a support 42 of generally semi-cylindrical shape, including a heel 43, forming a half-collar, carried by the tube 22. The two half-collars 43 are assembled together by means of connection members of a known type, for example screws, disposed in holes 44 in radial fins 46 of each collar. These half-collars 43 can be displaced axially along the tube 22 by sliding over a portion of the external surface thereof including a flat 47 extending longitudinally and locking the half-collars 43 from rotation by interaction of their shapes. The longitudinal displacement of the half-collars 43 is limited by two shoulders 48, 49 constituting the longitudinal ends of each flat 47 and forming stops for positioning the supports 42 with respect to the staple holder 32.

The supports 42 are made for example of a relatively elastic metallic material in order to be able to space apart, approximately radially, distal ends carrying the anvil sectors 40a, 40b. Such spacing facilitates the placing of the prosthesis 24 and of the vessel 26 over the tube 22, between the latter and the supports 42. The supports 42, in the spaced-apart position, are shown in dashed lines in FIG. 1.

A locking hoop 50 allows the sectors of the anvil to be assembled together after having previously disposed the organic ducts to be stapled over the internal part of the staple inserter and having positioned the supports 42 opposite the staple holder (half-collars 43 abutting against the distal shoulder 48). The hoop 50 can be displaced axially along the external surface of the supports 42. A lug 52 disposed radially on the internal wall of the hoop 50 interacts with a longitudinal groove 54 in one of the supports 42 to guide the hoop 50 between the heels 43 forming the half-collars and the distal ends of the supports 42 carrying the anvil sectors 40a, 40b. The hoop 50 is made of a relatively elastic material, for example a plastic material, so as to make it possible to assemble the anvil sectors 40a, 40b by wedging the hoop around the supports 42 at the anvil sectors 40a, 40b.

Figure 3:
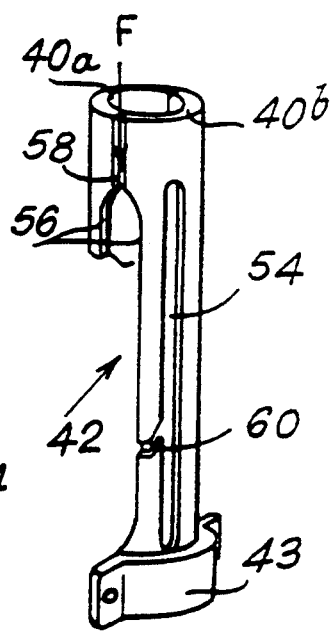
FIG. 3 is a partial perspective view of protruding supports defining an anvil.

FIG. 3 is a partial schematic view of the supports 42 allowing it to be understood how the hoop 50 is mounted thereon. The supports 42 are first mounted on the staple inserter and assembled together by their heels 43 which form half-collars. The hoop 50 is then placed around the supports while engaging the lug 52, along the arrow F, in a longitudinal groove 58 common to the two supports 42. By displacing the hoop 50 towards the heels 43 of the supports 42, the lug is brought into longitudinal recesses 56 of the supports 42 which face each other. Finally, the lug 52 is brought to the level of a groove 60 communicating with the guide groove 54, which allows lug 52 to be engaged in the latter.

Now will be explained the fixing and mounting of the handle 30 and the stapling wing nut 34.

The two half-handles 30a, 30b are extended at their ends on the one hand by half-sleeves 62a, 62b for supporting the wing nut 34, and on the other hand by half-sleeves 64a, 64b for fixing onto the tube 22. The two half-sleeves 62a, 62b of the handle 30 include two annular ribs 65 which interact with annular channels 66 of complementary shape in the internal wall of the wing nut 34, while allowing free rotation of the wing nut 34 on the handle 30. The proximal end of the tube 22 which is fitted into the half-sleeves 64a, 64b of the handle 30 includes an annular projection 67 for axial positioning of the hand 30 and which interacts with an annular groove 68 of complementary shape made on the internal surfaces of the half-sleeves 64a, 64b.

In order to mount the handle 30, the stapling wing nut 34 is first dispersed on a support. The two half-sleeves 62a, 62b for supporting the wing nut are then fitted into the cap 35 of the wing nut 34. This is done by juxtaposing joining edges 69a, 69b of the half-sleeves 62a, 62b which are symmetrically truncated, the effect of which is to form an angle between the two half-handles 30a, 30b. The proximal end 70 of the rod 37, of square cross-section, is engaged in a hole 71, of complementary shape, in the cap 35 of the wing nut 34. The proximal end of the tube 22, over which a sliding fastening hoop 72 has previously been placed, is disposed between the two half-sleeves 64a, 64b of the handle 30. The half-handles 30a, 30b are closed onto each other and the fastening hoop 72 is slid over the external surfaces of the two half-sleeves 64a, 64b, wedging them together.

FIGS. 4 to 8 show a first embodiment of the staple holder 32 and of the corresponding anvil 40. The staple holder 32 and the anvil 40 are disposed vertically in FIG. 4. The staple holder 32 consists of two flanges 82, 84 firmly attached to the tube 22 and carrying a rotating pin 85 onto which is fixed a disc 86 which can rotate between the flanges 82, 84. The disc 86 is pushed onto the median zone of the pin 85 which includes a portion 88 with an irregular surface ensuring better connection between the disc 86 and the pin 85. The pin 85 is connected at one end thereof of square cross-section to the drive nut 39.

The flange 82 is positioned axially inside the tube 22 between an edge 90, delimiting the opening of the cap 27, and the disc 86. The flange 84 is positioned inside the tube 22 between a shoulder 91, corresponding to an increase in the internal space of the tube 22, and the disc 86. The flanges 82, 84 are positioned angularly with respect to the tube 22 by means of axial projections 92, 93 which interact with notches 92a, 93a of complementary shape. Also, flanges 82, 84 are respectively arranged on the edge delimiting the opening of the cap 27 and on the shoulder 91 of the tube 22.

Figure 6:
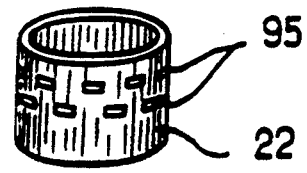
FIG. 6 is a partial perspective view of an internal part of the staple inserter showing the arrangement of staple ejection orifices.

Staples 94 are disposed flat between opposite faces of the disc 86 and of flanges 82, 84, so as to constitute two superimposed rings of staples. Each ring of staples 94 includes ten staples distributed over the entire circumference of the tube 22. Points of the staples 94 project radially outside the tube 22, through orifices 95 therein. FIG. 6 shows how the orifices 96 of the tube 22 are arranged in two superimposed rings, so that the orifices 95 of one ring are staggered with respect to the orifices 95 of the other ring.

Figure 5:
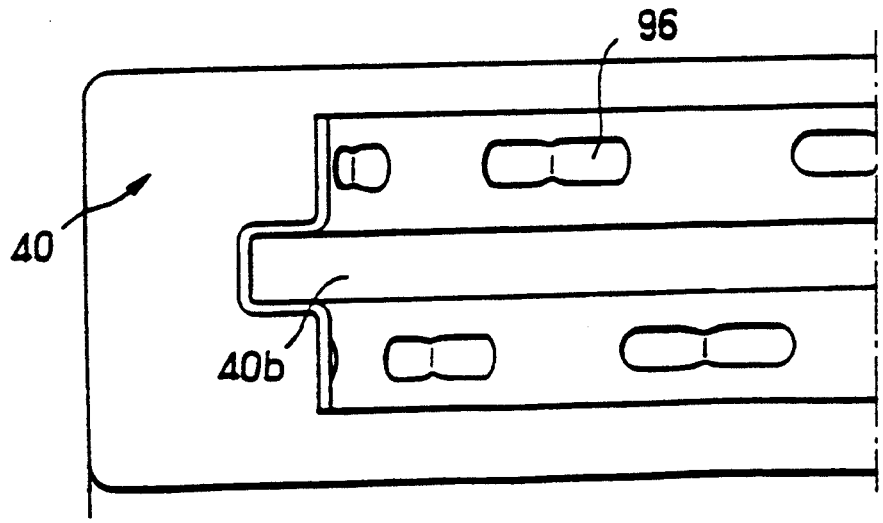
FIG. 5 is a view of half of an anvil sector along the arrow 5 in FIG. 4.

FIG. 5 shows anvil sector 40b which includes cavities 96, of known shape, intended to receive the points of the staples in order to hold them back during stapling.

Figure 4:
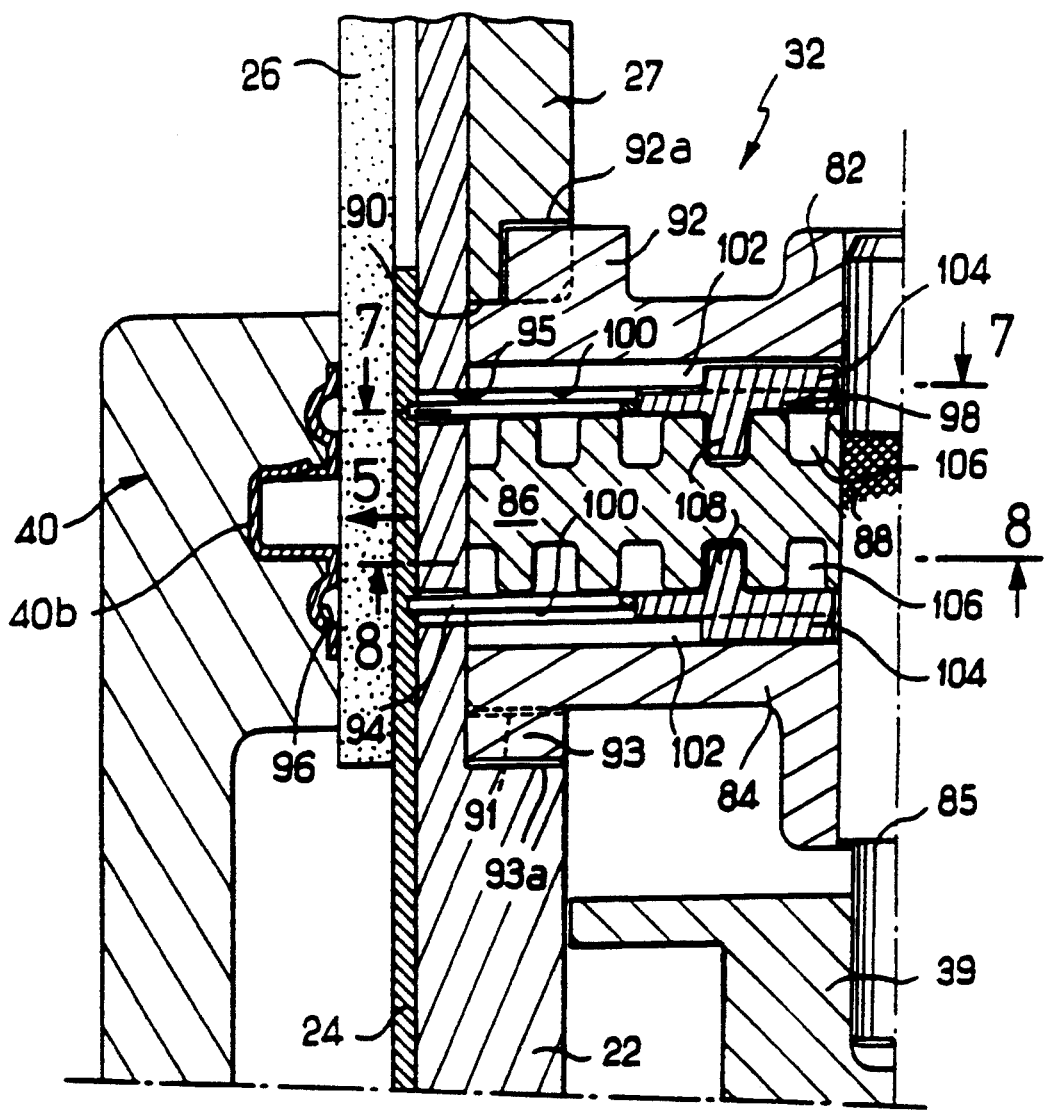
FIG. 4 is a partial longitudinal section of the staple holder.
Figure 7:
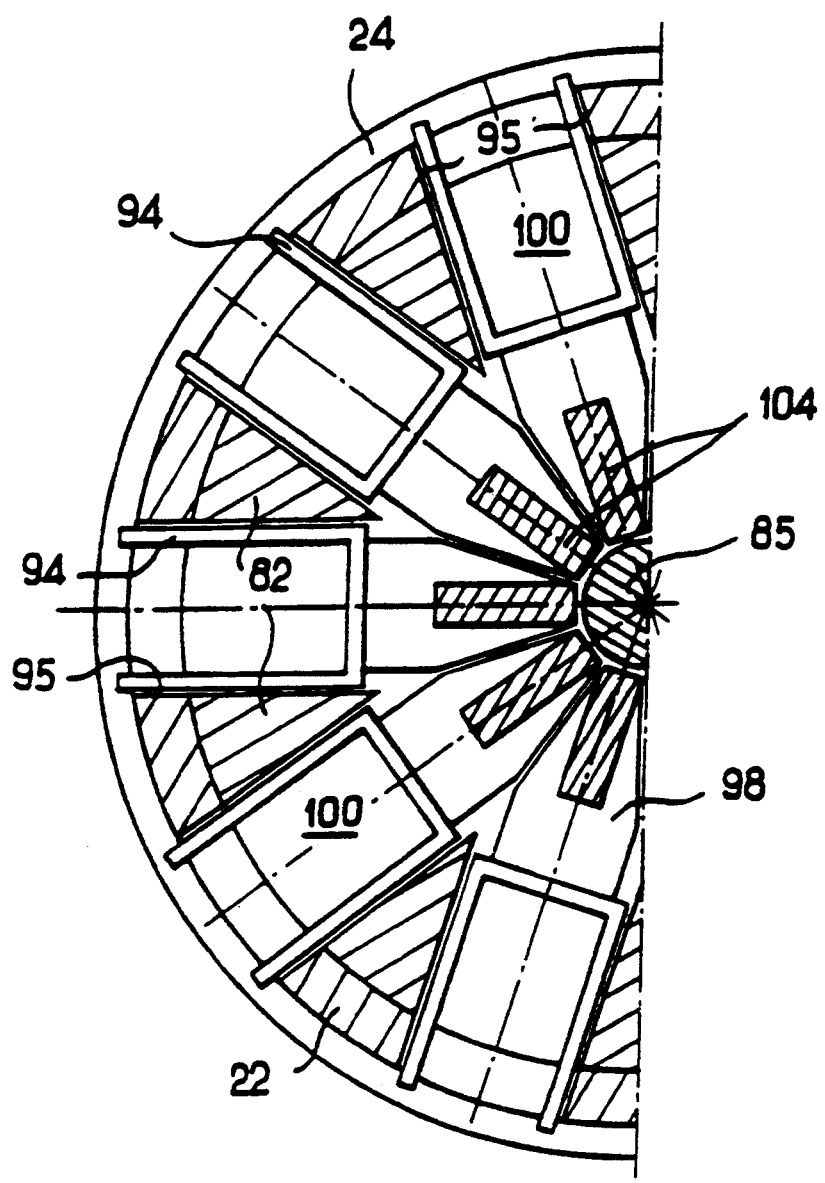
FIG. 7 is a section along the line 7—7 in FIG. 4.

The means for ejecting the staples 94 will now be described. In this connection, reference will be made to FIGS. 4, 7 and 8. FIGS. 4 and 7 show that each staple 94 is ejected by a hammer 98 of generally flat shape. The hammers 98 are disposed in rings between the opposite surfaces of the disc 86 and of flanges 82, 84. The flanges 82, 84 include, on the surfaces thereof opposite the disc 86, means for guiding the staples 94 and means for guiding the hammers 98. The means for guiding the staples 94 consist of radially extending recesses 100 in the surfaces of the flanges 82, 84, in which recesses the staples are housed. The means for guiding the hammers 98 consist of radial grooves 102 arranged on the surfaces of the flanges, in the middles of the respective recesses 100, which interact with guiding projections 104 disposed on respective faces of the hammers 98. The disc 86 includes means for driving the hammers 98, which means consist of spiral channels 106, at constant pitch, arranged symmetrically in opposite faces of the disc. The spiral channels 106 interact with respective drive projections 108 disposed on respective faces of the hammers 98.

Figure 8:
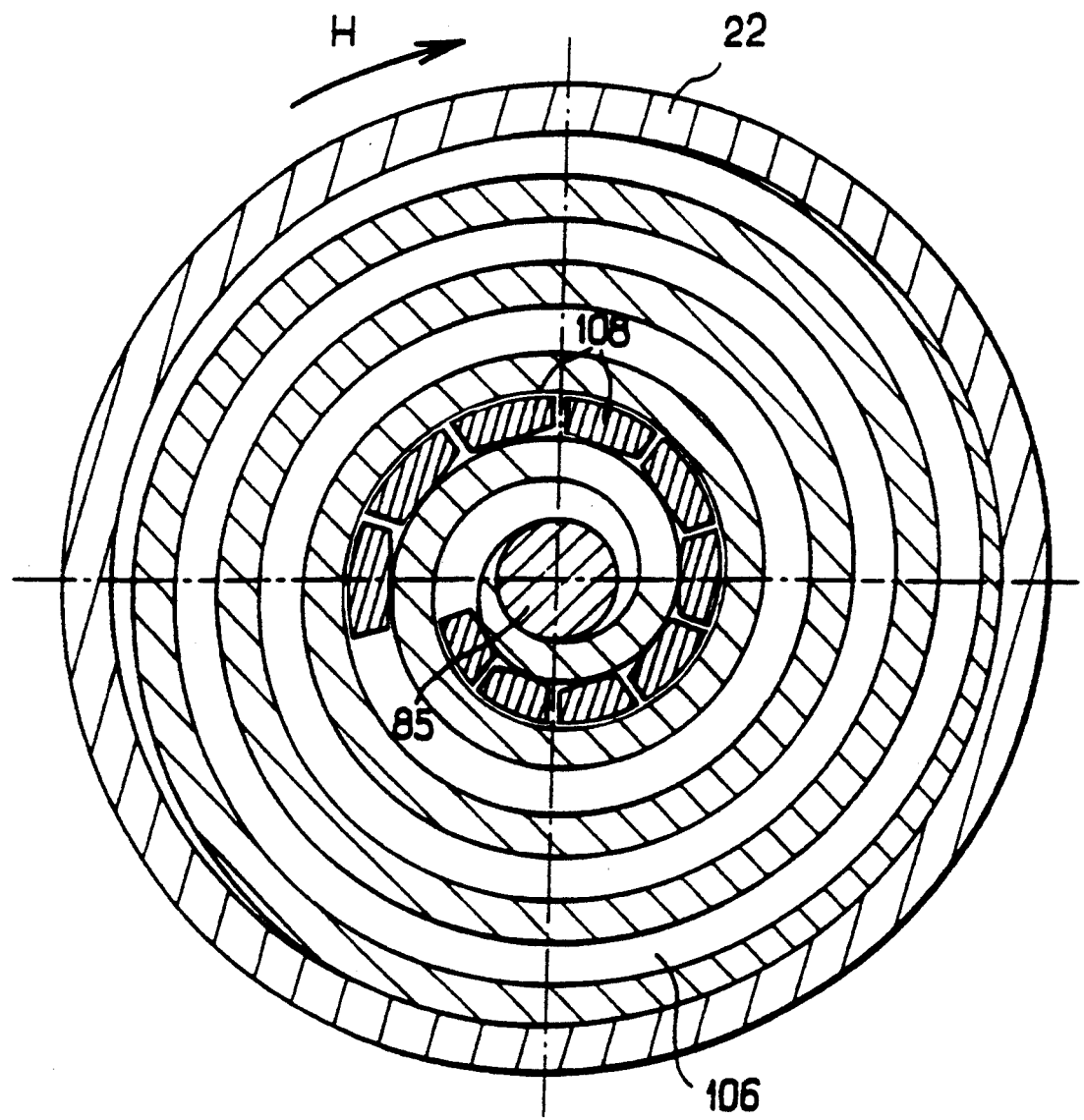
FIG. 8 is a section along the line 8—8 in FIG. 4.

FIG. 8 shows how the projections 108 of the hammers 98 are disposed in the spiral ribs 106 of the disc 86. There are ten projections 108, corresponding to ten hammers 98, which simultaneously eject each ring of ten staples. The hammers 98 are set in their initial position, before stapling, at the center of the disc 86. The position of the projection 108 on each hammer 98 depends on the angular position of the latter in the staple holder. As the spiral channel 106 has a constant pitch, the rotation of the disc 86 in the clockwise direction, along arrow H in FIG. 8, simultaneously drives all the hammers 98, displacing them radially by an equal distance.

The mounting of the staple holder 32 according to this first embodiment will now be described. In a first step, the cap 27 is placed on a support. There are then successively assembled the first flange 82, on the cap 27, the disc 86 fixed on the pin 85, and the second flange 84. The hammers 98 are next introduced into the staple holder 32. Since the position of the drive projection 108 on each hammer 98 is a function of the angular position of the latter in the staple holder 32, it is expedient to dispose the various hammers 98 in the staple holder 32 in a well-defined order. For this purpose, the first step is introducing the first hammer 98 of the series into the staple holder by engaging the drive projection 108 in the spiral channel 106, through the periphery of the disc 86, at a recess 100 for guiding the staples. The same procedure is repeated with the other hammers 98 of the series, in the order in which they are disposed in the staple holder. All the hammers 98 are set in their initial position, at the center of the disc 86, by rotating the disc 86 fully in the counterclockwise direction. The cap 27/staple holder 32 assembly is then disposed in the distal end of the tube 22. The means for axial positioning and rotational positioning of the flanges 82, 84 which were described hereinabove ensure the correspondence between the orifices 95 for ejecting the staples from the tube 22 and the recesses 100 for guiding the staples 94. The staples 94 are introduced into the staple holder 32 through the orifices 95 while orienting their points outwards and while placing the crosspiece of each staple 94 in contact with the corresponding hammer 98. The length of the hammers 98 is such that, when they are in the initial position, the points of the staples extend slightly outside the tube 22. Thus, the points of the staples 94 press slightly into the wall of the prosthesis 24, without passing through it, so as to hold it on the tube 22.

Figure 9:
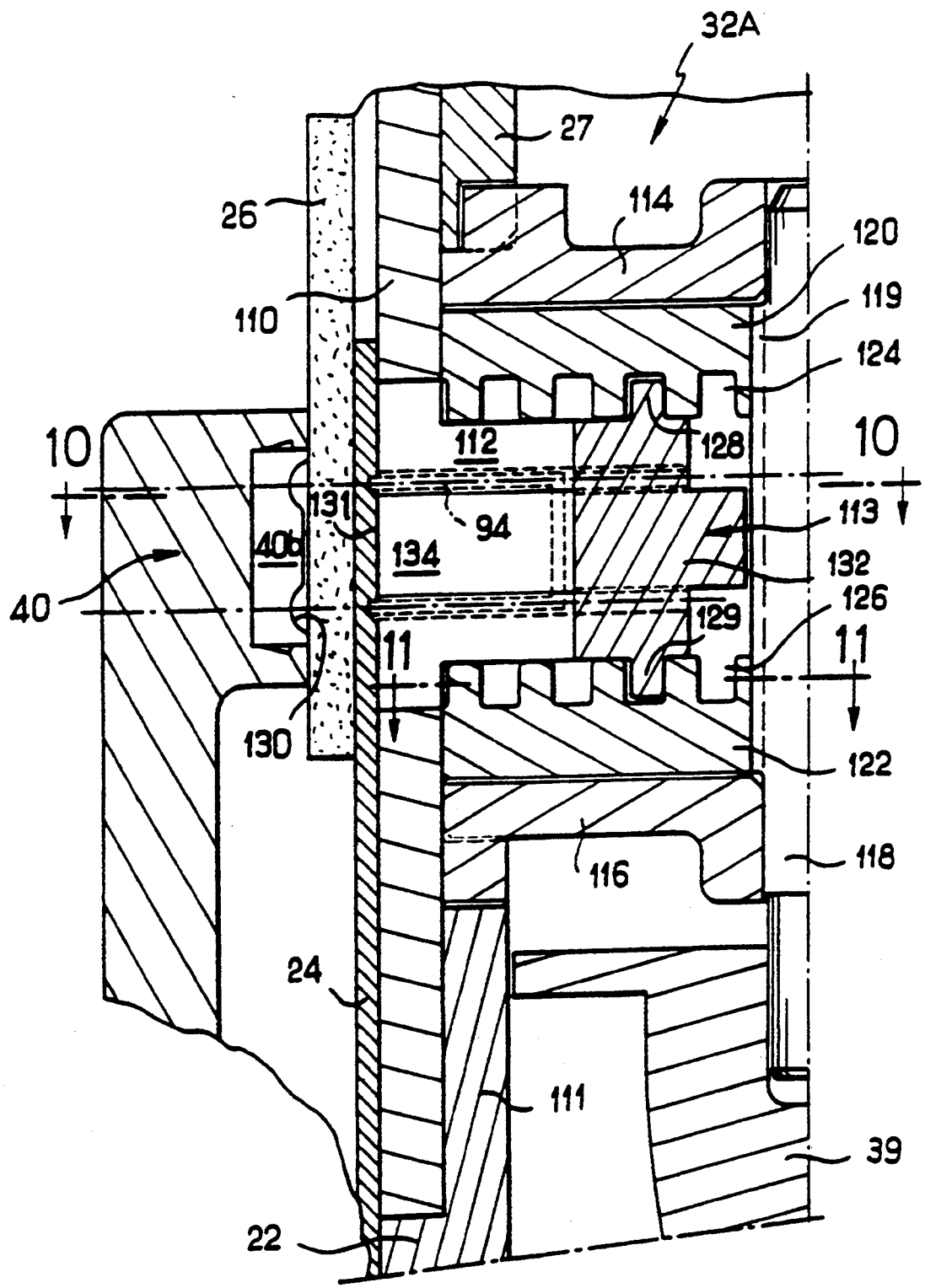
FIG. 9 is a partial longitudinal section of a varied embodiment of the staple holder.
Figure 10:
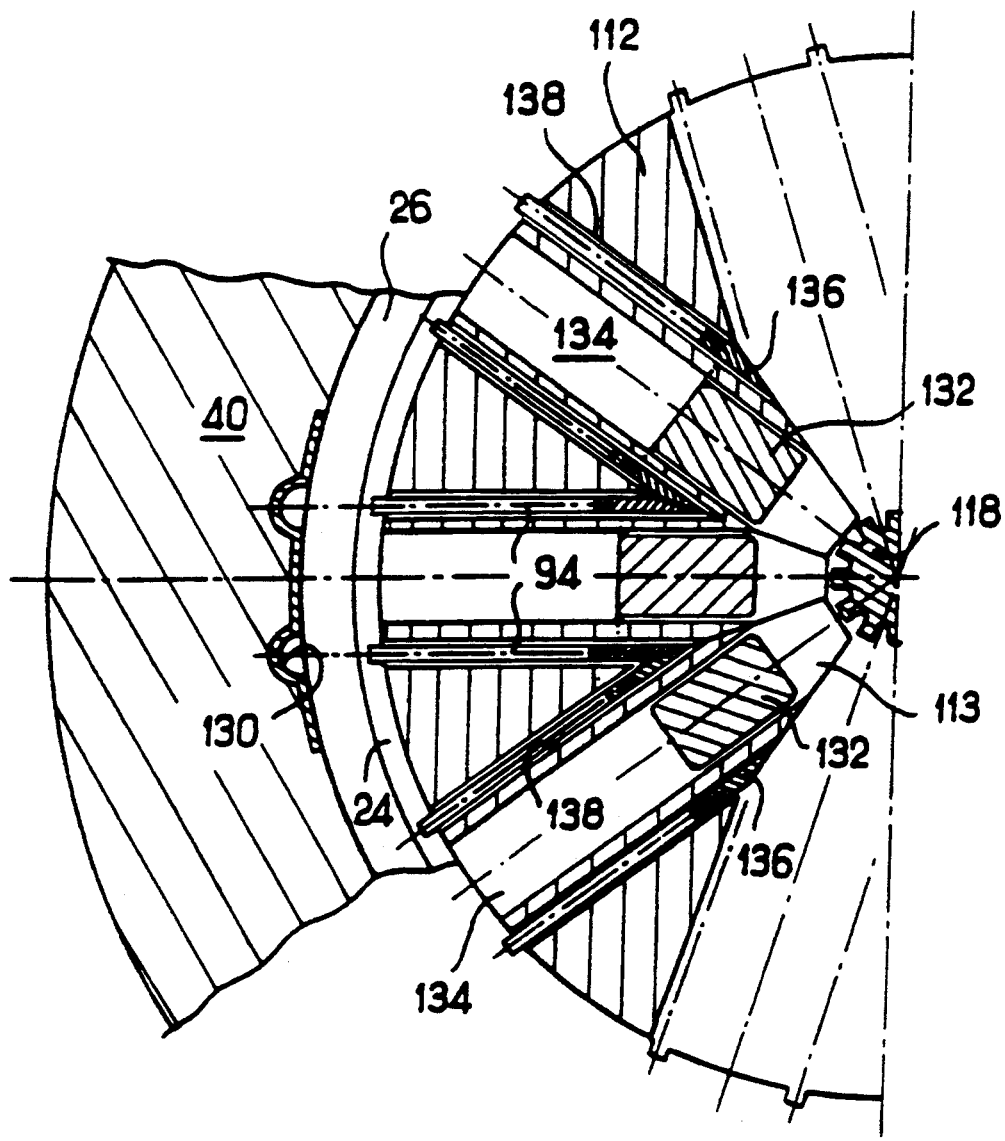
FIG. 10 is a section along the line 10—10 in FIG. 9.
Figure 11:
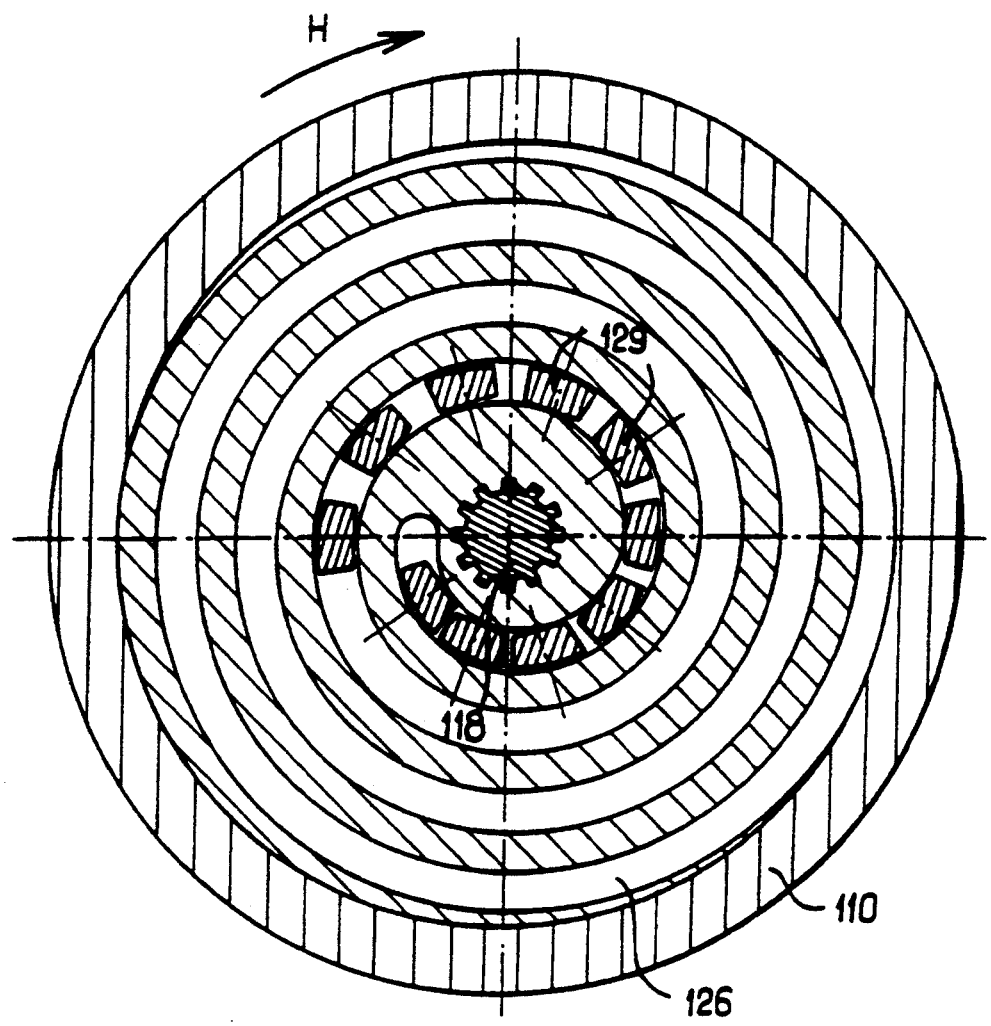
FIG. 11 is a section along the line 11—11 in FIG. 9.

FIGS. 9 to 11 show a staple holder 32A according to a second embodiment. In this case, the holder includes a single ring of staples 94 whose crosspieces are oriented axially. In contrast to the previous embodiment, the staple holder 32A is disposed in a sleeve 110 which is pressed over the distal end of the tube 22, at a constriction 111 of the external wall thereof. The sleeve 110 includes a collar piece 112, consisting of a single piece, which projects inside the sleeve, and which is used as a support for various elements of the staple holder 32A. As in the case of the first embodiment, the staple holder 32A has two flanges 114, 116 used as a support for a rotating pin 118 connected to the drive nut 39 by interaction of their shapes. In the second embodiment of the staple holder 32A, the cap 27 is pressed into the sleeve 110 and the flanges 114, 116 are positioned axially and angularly with respect to the tube 22 in a manner similar to that of the first embodiment of the staple holder 32. Conversely to the first embodiment, two discs 120, 122 for driving hammers 113, which discs are fixed onto the pin 118 by interaction of their shapes with axial ribbings 119 in the pin, are disposed on either side of the collar piece 112. Discs 120, 122 each carry on a face thereof opposite a respective face of the collar piece 112, a spiral channel 124, 126, of constant pitch. Drive channels 124, 126 are symmetrical to each other and interact with respective drive projections 128,129 of each hammer 113.

Figure 12:
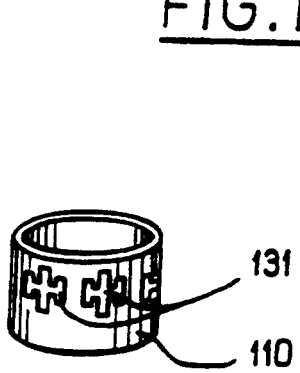
FIG. 12 is a partial perspective view of an internal part of the staple inserter showing the arrangement of staple ejection orifices according to a variant of the invention.
Figure 13:
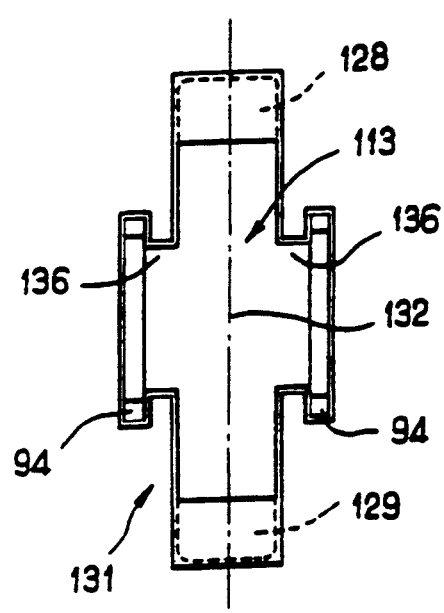
FIG. 13 is a front view of a staple ejection orifice according to such variant of the invention.

In FIG. 9, the staple holder 32A is disposed vertically and the hammers 113 are in their initial position before stapling, i.e. at the center of the staple holder 32A. The anvil 40 is in this case adapted in order to be able to receive the staples 94 whose crosspieces are oriented axially with respect to the staple holder. Anvil 40 has cavities 130 of known shape, intended to fold the points of the staples 94 during stapling. The staple holder 32A includes ten hammers 113 each ejecting two staples 94 through orifices 131. FIG. 12 shows how the orifices 131 for ejecting the staples are disposed entirely around the sleeve 110. FIG. 13 shows in more detail an orifice 131 having generally a cross shape. The two lateral branches of the cross-shaped orifice 131 have T-shaped ends, through each of which one staple 94 is ejected. Similarly, each hammer 113 has a general cross shape when viewed facing an orifice 131 for ejecting the staples. Each hammer has a central body 132 represented vertically in FIGS. 9 and 13. The central body 132 is guided in a radial guide hole 134 in the collar piece 112. The central body 132 is fitted at its middle with two lateral branches 136 whose ends are T-shaped like the contour of the orifices 131. The ends of the branches 136 of each hammer are engaged in slideways 138 made in the collar piece 112 of the sleeve 110 and extending radially parallel to the holes 134 for guiding the central body 132 of the hammers 113. The staples 94 are disposed in the slideways 138 such that their crosspiece is in contact with the ends of the branches 136 of the hammers 94.

FIG. 11 shows the spiral channel 126 in which the drive projections 129 of the hammers 113 are received. It is seen that the position of the projections 128, 129 on the central body 132 of the hammers 113 depends on the angular position of the hammer 113 in the staple holder, as in the case of the first embodiment of the staple holder.

The staple holder 32A is mounted in accordance with the general principles previously described with regard to the first embodiment. The cap 27 is disposed in a support, then there are successively assembled the flange 114, the pin 118 with ribs, a first drive disc 120, the sleeve 110, a second drive disc 122 and finally the second flange 116. The sleeve 110 and the staple holder 32A are disposed on the distal end of the tube 22, and while rotating the discs 120, 122 in the counterclockwise direction, the hammers are introduced through the orifices 131 in order. Finally, the staples 94 are disposed in the slideways 138 on either side of the hammer guide holes 134 in the collar piece 112.

As in the first embodiment of the staple holder, the points of the staples 94 project outside the internal part of the staple inserter so as to press into the wall of the prosthesis 24 without passing through it, in order to hold it axially on the staple inserter.

In both embodiments of the staple holder, the staple inserter is intended to be used with a prosthesis 24 previously positioned over the tube 22 approximately between the heels 43 of the supports 42 and the anvil 40. In order to position the staple inserter in the vessel 26, the anvil supports 42 are spaced apart in order to dispose the vessel 26 between the anvil 40 and the end of the prosthesis 24, at the staple holder 32. The supports 42 are then positioned axially and the anvil sectors are assembled together by means of the locking hoop 50. For a stapling operation, the operator grips the staple inserter by the handle 30 and rotates the stapling wing nut 34. The rod 37 drives the pin 85, 118 in rotation via the drive nut 39. The hammers 98, 113 are then driven radially towards the periphery of the tube 22 and eject the staples 94 against the anvil 40.

The staple inserter shown in FIGS. 14 to 21, with its axis X—X assumed to be horizontal, includes the following pieces, represented in exploded form in FIG. 14:
- a handle 201, consisting of two halves assembled along the plane of symmetry of the staple inserter by screws 202;
- a trigger 203 and its safety catch 204;
- a hollow central rod 205 and its annular operating button 206;
- a retention ring or hoop 207 and an annular nose 208;
- a retention ring or hoop 207 and an annular nose 208;
- a mounting hoop 209;
- a flexible tubular prosthesis 210 made of a biocompatible synthetic material, slightly pleated in concertia fashion;
- six jaws or sectors 211;
- in each jaw two staples 212 and a staple pusher 213 common to these two staples;
- a hook 214 for closing the jaws, and an arming lever 215.

Each half of the handle 201 has internally and at the rear thereof, an elastic clip 216 surrounding an orifice 217 and at the front thereof a guiding slot 218, an arc-shaped window 219 and vertical positioning ribs 220. The slot 218 includes, from the rear to the front, a slightly descending part, a sharply descending part and a horizontal part.

The trigger 203 is hinged on the handle around a spindle 221. An upper part of trigger 203 has a T-shape including branches 222 that project through the windows 219. The catch 204 is hinged on the handle around a spindle 223 between an approximately horizontal active position (FIGS. 15 to 17) at which catch 204 fits into a notch 224 in the trigger in order to lock it in an inactive position, and an approximately vertical (FIG. 18) retracted position which allows actuation of the trigger.

The rod 205 has an external diameter which is uniform over approximately its entire length, except at a front or distal part 225 thereof having an enlarged diameter. Rod 205 includes at a rear or proximal part thereof two annular channels 226, 227 spaced a small distance from each other, and rod 205 terminates at a rear end in a tip 228 on which the button 206 is fixed. A cylindrical stud 229 is half inserted into an orifice 230 in the rod 205 which includes, over the entire length thereof, an axial passage 231. The front end of the part 225 constitutes an anvil and has two rings of recesses 232 oriented axially (FIG. 21).

Figure 21:
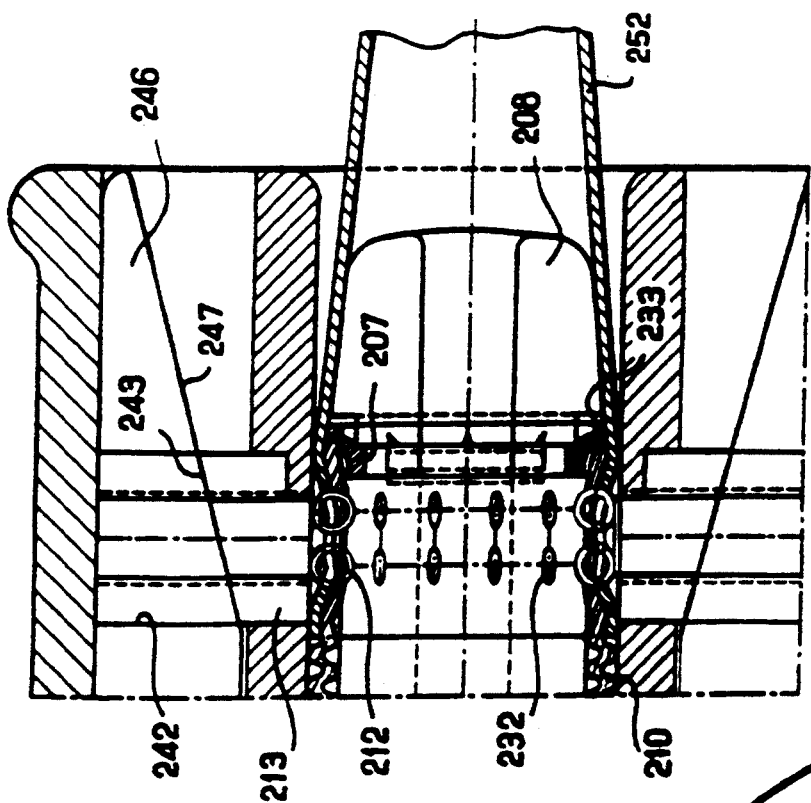
FIG. 21 is a partial axial section of a distal end part of the same sample inserter on an even larger scale.

As FIG. 21 shows more clearly, the retention hoop 207 is a flat band fixed to the distal end of the rod 205 by means of the nose 208. The latter is frusto-conical on the outside, converging towards the front, while the hoop 207 includes a ring of points 233 oriented obliquely forwardly and projecting radially with respect to the anvil 225.

The mounting hoop 209 is fixed into the handle by means of the ribs 220 and includes an axial bore 234 through which the rod 205 passes. The wall of this bore includes an axial groove 236 in which the stud 229 slides (FIG. 19), which ensures angular positioning of the rod 205 with respect to the handle. Rod 205 may be moved axially, by means of the button 206, either to an advanced position (FIG. 15), at which the button is adjacent to the handle, or to a pushed-back position (FIGS. 16 to 18). These two positions are precisely defined by the elastic entry of the clip 216 in the channel 226 or in the channel 227.

Figure 19:
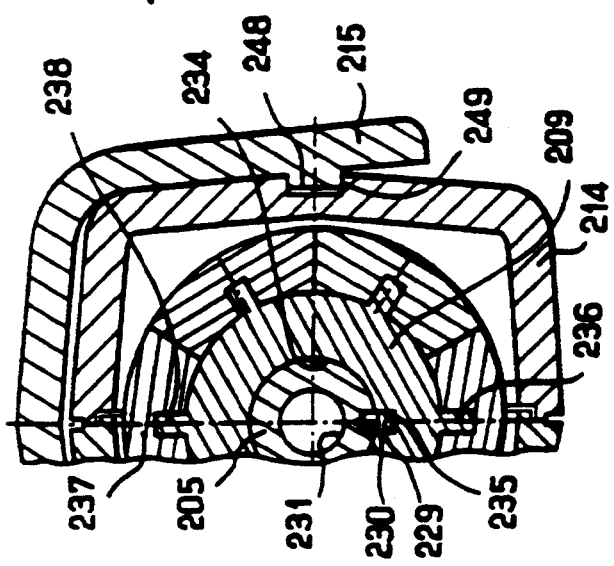
FIGS. 19 and 20 are half sections on an enlarged scale taken respectively along the lines 19—19 and 20—20 in FIG. 18.
Figure 20:
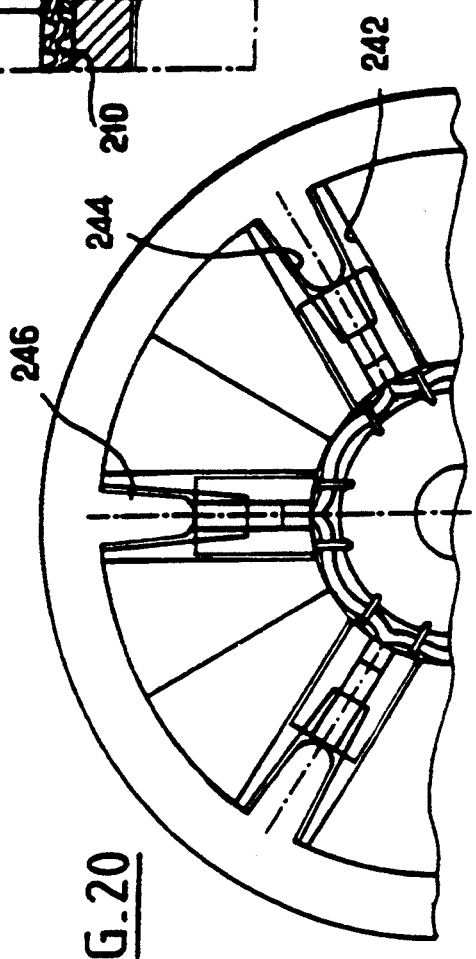

The front portion of hoop 209 is provided externally with six axial ribs 236 (FIGS. 14 and 19).

Each jaw 211, made of a plastic material, extends over an angle of 60°, has the general shape of a cylindrical sector and includes three molded parts:
- a rear part 237 delimited between two internal radial shoulders and including a median axial groove 238 (FIGS. 14 and 19), in order to ensure its axial and angular positioning on the mounting hoop 209;
- an intermediate part 239 protruding forwardly; and
- a front part 240 connected to part 239 by a hinge 241 which is deformable and, at rest, slightly divergent towards the front.

A radial slit 242 is made in the front part 240 of each jaw, in which slit a respective staple pusher 213 is guided so as to slide radially, the interior end of slit 242 receiving two parallel staples 212. The staples all have an axially oriented crosspiece and two points directed approximately towards the axis X—X. Each pusher includes an inclined external surface 243 forming a cam slope.

Each jaw furthermore has, along the parts 239 and 240, an axial groove 244 which is interrupted by the slit 242. In part 239, groove 244 is divided, approximately half way along its length, by a transverse rib 245.

Inside the hoop 214 are six axial ribs 246 sliding in respective grooves 244. In the front part of hoop 214 the ribs 246 have a height which decreases so as to define six cam slopes or surfaces 247 of the same inclination as the surfaces 243 of the staple pushers 213.

The arming lever 215 has an elongated shape with a U-shaped cross-section (FIG. 19). At its front portion lever 215 includes two internal stubs 248 (FIGS. 14 and 19) received in diametrically opposite recesses 249 provided in the hoop 214. In its rear portion the lever 215 includes two other stubs 250 guided in slots 218 in the handle, each branch of the U-shape has a deep cutout 251.

The use of this staple inserter includes four steps, respectively illustrated in FIGS. 15 to 18.

First, the lever 215 is pushed rearwardly so as to lead the hoop 214 over the parts 239 of the six jaws 211 until hoop 214 abuts against the ribs 245. In this position, because the shape of the slots 218 is inclined towards the front, the rear of the lever 215 is raised. In addition, the button 206 is driven in towards the handle, with the clip 216 engaged in the rear channel 226 of the rod 205, so that the anvil 225 projects far towards the front beyond the jaws, which are open. The surgeon may thus easily observe the introduction of the anvil into one extremity of a blood vessel 252 (FIG. 21) to be connected to the prosthesis 210, which is placed over the anvil 225. This introduction is facilitated by the frusto-conical shape of the nose 208, whose maximum diameter is substantially equal to that defined by the points 233. Preferably, to the same end, the front end part of the prosthesis is smooth, that is to say not pleated. During this introduction, the points 233, which penetrate into the thickness of the front end of the prosthesis without passing through it, prevent any backward movement of the prosthesis.

When the anvil has penetrated the vessel 252 sufficiently in order for the vessel to cover the zone of the two rings of recesses 232, the surgeon, holding the button 206, pushes the handle, and therefore the rest of the staple inserter, forwards, until the clip 216 engages in the front channel 227 of the rod 205, and therefore achieves the situation illustrated in FIG. 16, which only differs from that in FIG. 15 in that the recesses 232 of the anvil are situated exactly in line with the points of the twelve staples 212 ready in the six jaws 211.

The following step (FIG. 17) consists in pushing the arming lever 215 forwards, which pushes the hoop 214 in order to close the six jaws. This being done, the inclined parts of the slots 218 of the handle force the lever 215 to fold down progressively, until the two cutouts 251 cover the projecting arms 22 of the trigger 203. The front end of the hoop 214 is then situated at a distance behind that of the jaws 211, with the slops 247 situated exactly opposite the slopes 243 of the staple pushers.

It then only remains to disengage the catch 204 and to press the trigger. The arms 222 then push the lever 215, and therefore the hoop 214, forwards, the two stubs 250 then being guided along the horizontal front part of the slots 218. The interaction of the slopes 247 and 243 causes the radial displacement inwardly of the six pushers 243, and therefore the simultaneous centripetal ejection of the twelve staples that thus pass through the vessel and the prosthesis and are bent in the recesses 232. The final position is that represented in FIG. 21.

In order to retract the staple inserter, the arming lever 215 is pulled back. The consecutive backward motion of the hoop 214 frees the six jaws, which reopen by simple elasticity. The inclination towards the front of the points 233 then allows the anvil to leave the stapled zone and then the prosthesis towards the rear, simply by pulling the handle 201.

The embodiment in FIGS. 22 and 23, which also uses cams sliding axially for ejecting the staples, but which is of a "centrifugal" type as in the case of FIGS. 1 to 13, will now be described.

A handle 301/trigger 303/catch 304 assembly is still present, but the openings 218 and 219, the ribs 220 and the slip 216 of the preceding embodiment are not provided. The handle has, in the axis X—X, a rear orifice 305 and a front duct 306 of larger diameter in which the rear end, of reduced diameter, of a main tubular body 307 is fixed. At the front end of body 307 a front tubular body 308 of larger diameter is fixed by means of a screw nut 307A. A hollow rod 309 slides in the assembly 307308 and is urged rearwardly thereof by a helicoidal spring 310. The rear end of rod 309, inside the handle, has a step 311 which bears on an upper, forked, end of the trigger 303.

The front end of the body 308 has six radial slits 312 for guiding respective staple pushers 313 and for receiving two parallel staples 314 with crosspieces oriented axially and with points directed approximately radially outwardly. An ejector 315 slides in the body 308 and has a cylindrical rear part and a frusto-conical front part. Such front part defines a cam slop 316 of the same gradient as radially internal surfaces 317 of the staple pushers. The ejector 315 includes a central passage 318.

A hoop 319 for retention of a prosthesis 320 is fixed at the front end of the body 308, and a rear face of hoop 319 defines the fronts of the slits 312. Hoop 319 includes a ring of points 321 inclined forwardly. The prosthesis is placed over the body 308, and a smooth front end of the prosthesis covers the slits 312 and the points 321, which penetrate into the thickness of the prosthesis without passing therethrough.

A nose 322 is mounted so as to slide with respect to the hoop 319 by means of several axial screws 323 screwed in the latter. Nose 322 includes a peripheral skirt with axial slots defining a series of flexible tongues 324 directed rearwardly. In the ready position of the stapler, illustrated in the lower half of FIGS. 22 and 23, the nose is pressed flat against the hoop 319. A central bore 325 of the nose converges towards the front along the same gradient as the cone 316 and extends inner conical surface 326, with the same gradient, of the hoop 319. Rear ends of the tongues 324 cover the front end of the prosthesis.

The staple inserter also includes six jaws 327 each fitted at their front end with an anvil sector 328 provided with two axially oriented recesses 329. Each jaw is a protruding cylindrical sector connected by a thin hinge 330 to a common rear tubular support 331 which slides over the main body 307. Each sector is urged outwardly into an open position by a leaf spring 332.

The support 331 is extended towards the rear by an appendage 333 from which a lug 334 leads towards the axis X—X. An L-shaped security brake 335 is hinged on lug 334 and includes a branch 336 which is pushed by a spring towards a horizontal position and a radial branch 337. The latter extends outwardly through a slit in the appendage 333 and terminates in an oblique surface inclined inwardly and forwardly.

A closure hoop 338 is slidable on the set of jaws 327, on the support 331 and on the appendage 333.

When the support is in a rear position which is not represented, with the hoop 338 ready on the support 331, the surgeon sees the prosthesis and the nose 322 and may force this into vessel 339 whose extremity easily passes over the front part of the prosthesis by virtue of the tongues 324. The surgeon then presses the support 331 forwardly. When this reaches a front stop, which is not represented, the recesses 329 of the anvil are situated exactly in the planes of the staples 314, and the brake 335 catches in front of the front face of the handle 301 (FIG. 22). The situation is then that represented in the lower half of FIGS. 22 and 23.

The surgeon then pushes the hoop 338 as far as its extreme front position, defined by an end stop 340 of the jaws, which closes the jaws.

Finally, the surgeon frees the catch 304 and presses the trigger 303. The front end of trigger 303 pushes the rod 309 forwards, compressing the spring 310, and rod 309 pushes the ejector 315. The cone 316, which was exactly opposite the surfaces 317 of the six pushers, displaces the latter radially outwardly by a cam effect, which produces simultaneous stapling of the prosthesis and the vessel by the twelve staples.

Simultaneously, the front end of the cone 316 comes into contact with the conical bore 325 in the nose 322 and pushes the latter forwardly until the cone abuts against the conical bore 326 of the hoop 319. As the upper halves of FIGS. 22 and 23 show, this displacement of the nose frees the tongues 324 which elastically return to a position parallel to the axis X—X.

This allows the staple inserter to be retracted rearwardly, but it is first of all necessary to push back the support 331, which is only possible when the jaws are in the open position by virtue of the presence of the brake 335. In fact, it is necessary initially to push back fully the hoop 338. When hoop 338 arrives on the appendage 333, it retracts the radial branch 337 of the brake 335, and the latter tilts, along the arrow f. It is then, and only then, possible to push back the support 331, with the jaws consequently open, to then retract the staple inserter. This avoids the risk of the surgeon accidentally pushing the support 331 backwards when the jaws are closed, which could have the effect of tearing the stapled zone of the vessel 339.

It should be noted that in this embodiment, as in that in FIGS. 14 to 21, the staple inserter includes, over its entire length, a continuously open duct, which allows a catheter or a fluid to pass.

We claim:

1. A surgical staple inserter assembly for joining two ducts including a vessel and a tubular vessel prosthesis, said assembly having a longitudinal axis, a proximal end portion and a distal end portion and comprising:
   an internal part to be received inside the ducts and an external part to remain outside the ducts;
   one of said internal and external parts including a staple holder containing a series of staples, each said staple having two points joined together by a crosspiece, said staples being disposed in at least one ring arranged concentrically of said axis with said points oriented radially of said axis, said staple holder including members to eject said staples;
   the other of said internal and external parts including an anvil;
   means for effecting a relative movement radially of said axis between said anvil and said staple holder between a radially expanded position and a radially contracted position;
   a tubular vessel prosthesis placed over a portion of said internal part; and
   point members projecting from said internal part and penetrating into a wall of said prosthesis.

2. A staple inserted assembly according to claim 1, wherein said point members penetrate into a smooth distal end part of said prosthesis adjacent said distal end portion.

3. A staple inserter assembly according to claim 1, wherein said internal part includes said staple holder, and said points of said staples are oriented radially towards said external part and form said point members penetrating into said wall of said prosthesis.

4. A staple inserter assembly according to claim 1, wherein said point members are firmly attached to said internal part.

5. A staple inserter assembly according to claim 4, wherein said point members are inclined toward said distal end portion.

6. A staple inserter assembly according to claim 1, wherein said internal part includes a nose member having a proximal part which has a diameter that is selectively variable between a first diameter which is greater than the diameter of said prosthesis in a ready position of said nose member and a second diameter which is less than said diameter of said prosthesis when said staples are to be ejected.

7. A staple inserter assembly according to claim 6, wherein said nose member is mounted to be axially slidable at a distal end portion of said internal part, said proximal part of said nose member includes a series of radially elastic tongues which cover a distal end of said prosthesis in said ready position of said nose member, and said internal part further includes a pusher to push said nose member forwardly approximately at a moment when said staples are to be ejected.

8. A staple inserter assembly according to claim 1, wherein said external part includes a sector support, at least two sector members supported by said support and displaceable approximately radially between a radially expanded position and a radially contracted position, a contracting member mounted to move said sector member to said radially contracted position, and a displacer to displace said support axially with respect to said internal part when said sector members are in said radially expanded position.

9. A staple inserted assembly according to claim 8, wherein said contracting member comprises a sliding hoop.

10. A staple inserter assembly according to claim 9, wherein said external part further includes a stop defining an axially forward position of said support.

11. A staple inserter assembly according to claim 9, further comprising a non-return brake to brake axial movement of said support, and means for releasing said brake upon said sector members being displaced to said expanded position.

12. A staple inserter assembly according to claim 1, wherein said members to eject said stapes comprise radially guided staple pushers, and further comprising a driver to drive said pushers.

13. A staple inserter assembly according to claim 1, wherein said external part includes said anvil.

14. A staple inserter assembly according to claim 1, wherein all of said staples are disposed in a single ring arranged concentrically of said axis, and said crosspieces of said staples are oriented to extend parallel to said axis.

15. A staple inserter assembly according to claim 1, comprising a central passage extending over the entire length of said assembly.

16. A surgical staple inserter assembly for joining two ducts including a vessel and a tubular vessel prosthesis, said assembly having a longitudinal axis and comprising:
   an internal part to be received inside the ducts and an external part to remain outside the ducts;
   one of said internal and external parts including a staple holder containing a series of staples, each said staple having two points joined together by a crosspiece, said staples being disposed in at least one ring arranged concentrically of said axis with said points oriented radially of said axis, said staple holder including members to eject said staples;
   the other of said internal and external parts including an anvil;

means for effecting a relative movement radially of said axis between said anvil and said staple holder between a radially expanded position and a radially contracted position; and means for effecting a relative movement between said staple holder and said anvil along said axis in said radially expanded position.

17. A surgical staple inserter assembly for joining two ducts including a vessel and a tubular vessel prosthesis, said assembly having a longitudinal axis, a distal end portion and a proximal end portion and comprising:

an internal part to be received inside the ducts and an external part to remain outside the ducts;

one of said internal and external parts including a staple holder containing a series of staples, each said staple having two points joined together by a crosspiece, said staples being disposed in at least one ring arranged concentrically of said axis with said points oriented radially of said axis, said staple holder including members to eject said staples;

the other of said internal and external parts including an anvil;

means for effecting a relative movement radially of said axis between said anvil and said staple holder between a radially expanded position and a radially contracted position;

a tubular vessel prosthesis placed over a distal end portion of said internal part;

a nose member at said distal end portion and including a proximal part having a tapered member to easily pass a vessel end over a distal part of said prosthesis; and means for radially varying a diameter of said tapered member between a first diameter which is greater than the diameter of said prosthesis in a ready position of said nose member and a second diameter which is less than said diameter of said prosthesis when said staples are to be ejected.

18. A surgical staple inserter assembly for joining two ducts including a vessel and a tubular vessel prosthesis, said assembly having a longitudinal axis and comprising:

an internal part to be received inside the ducts and an external part to remain outside the ducts;

one of said internal and external parts including a staple holder containing a series of staples, each said staple having two points joined together by a crosspiece, said staples being disposed in at least one ring arranged concentrically of said axis with said points oriented radially of said axis and with said crosspiece of each said staple having a dimension axially of said axis greater than a peripheral dimension thereof, said staple holder including members to eject said staples;

the other said internal and external parts including an anvil;

means for effecting a relative movement radially of said axis between said anvil and said staple holder between a radially expanded position and a radially contracted position; and a tubular vessel prosthesis placed over a distal portion of said internal part.

19. A staple inserter assembly according to claim 18, wherein said crosspieces of said staples are oriented to extend parallel to said axis.

* * * * *